United States Patent [19]

Finney

[11] Patent Number: 4,820,262

[45] Date of Patent: Apr. 11, 1989

[54] URETERAL STENT

[75] Inventor: Roy P. Finney, Bayport, Fla.

[73] Assignee: Medical Engineering Corporation, Racine, Wis.

[21] Appl. No.: 808,443

[22] Filed: Dec. 12, 1985

[51] Int. Cl.[4] .................................. A61M 27/00
[52] U.S. Cl. .................................. 604/8; 604/281
[58] Field of Search ........................ 604/8–10, 604/280–282; 623/12

[56] References Cited

U.S. PATENT DOCUMENTS

| 243,396 | 0/1881 | Pfarre | 604/281 |
|---|---|---|---|
| 1,060,665 | 5/1913 | Bell | 604/281 |
| 3,169,528 | 2/1965 | Knox et al. | 604/281 |
| 3,612,038 | 10/1971 | Halligan | 604/281 X |
| 3,631,848 | 1/1972 | Muller | 128/2.05 R |
| 3,674,014 | 7/1972 | Tillander | 128/1.3 |
| 3,805,794 | 4/1974 | Schlesinger | 604/103 X |
| 3,951,153 | 4/1976 | Leucci | 604/54 |
| 4,212,304 | 7/1980 | Finney | 604/8 |
| 4,307,723 | 12/1981 | Finney | 604/8 |
| 4,531,933 | 7/1985 | Norton et al. | 604/8 |

Primary Examiner—Dalton L. Truluck
Attorney, Agent, or Firm—Quarles & Brady

[57] ABSTRACT

An adjustable ureteral stent comprises an elongated, flexible tubular member with a hook at the proximal end, a generally straight elongated trimmable portion extending to the distal end and means for forming a hook at the distal end. In one embodiment the means is a second member which connects to the distal end of the first member and in another embodiment the means is a reinforcing wire or strip in the wall of the tubular member which when formed into a hook will retain that shape in the absence of a straightening force.

2 Claims, 2 Drawing Sheets

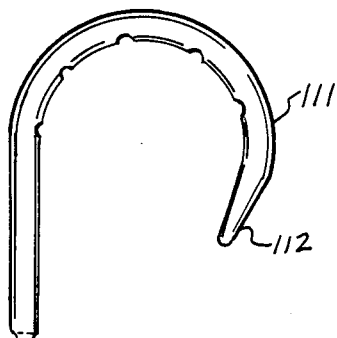
FIG. 4
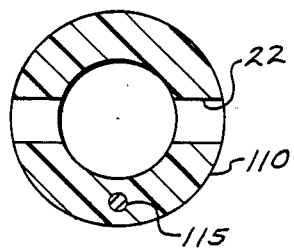
FIG. 5
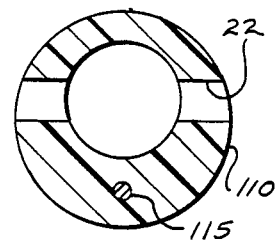
FIG. 6
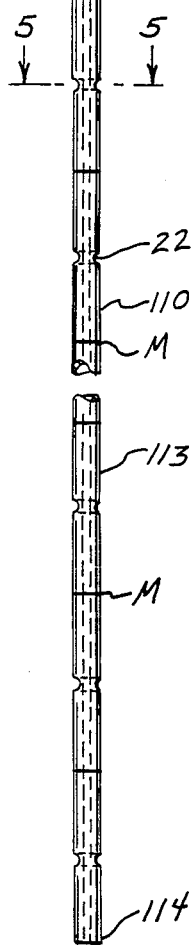
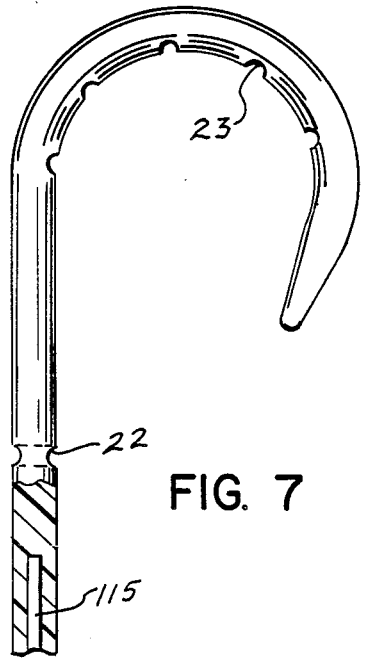
FIG. 8
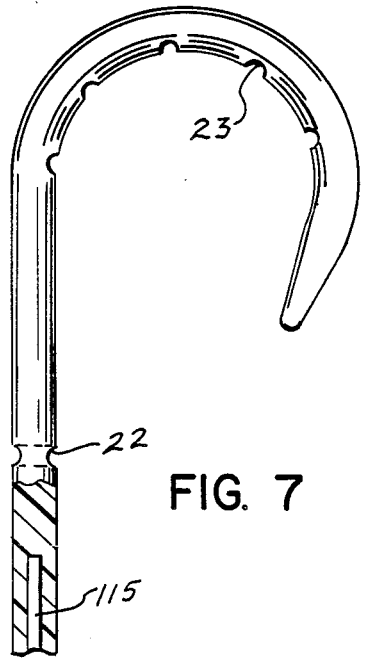
FIG. 7
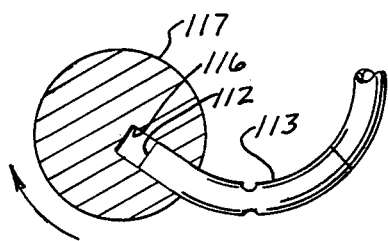
FIG. 9
FIG. 10
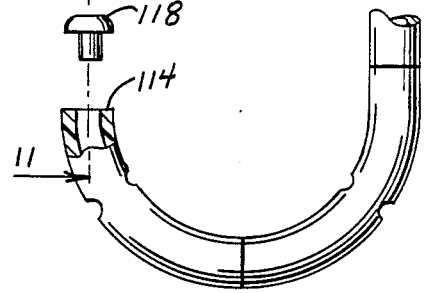
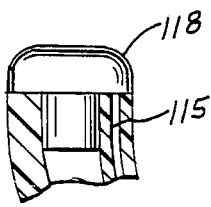
FIG. 11

URETERAL STENT

FIELD OF THE INVENTION

The present invention relates to ureteral stents. More particularly, it relates to a novel stent which can be readily reduced in length without increasing the tendency of the stent to migrate or to be expelled when implanted.

BACKGROUND OF THE INVENTION

Indwelling ureteral catheter stents or drainage tubes have been used to maintain urinary drainage. In the past, stents made of straight lengths of open end tubing have been used for this purpose and have provided good drainage for sustained periods of time. However, the use of such open end tubing has not been completely satisfactory. For example, in some instance, the tubing has migrated and in others it has been expelled.

Various attempts have been made to produce stents which do not have the problems which accompany the use of such tubing. For example, stents have been designed which are closed at one end (hereinafter referred to as the "proximal end") to facilitate passage into a body passage and which have at the other end (hereinafter referred to as the "distal end") a flange to make upward migration of the stent less likely. Another approach has been to provide the body of the stent with sharply pointed barbs which are designed to prevent downward migration and expulsion. However, such barbs increase the diameter of the stent making it more difficult to insert and in some instances can cause the stent to migrate outside the bladder.

In U.S. Pat. No. 4,212,304 issued July 15, 1979 and U.S. Pat. No. 4,307,723 issued Dec. 29, 1981, ureteral stents are disclosed which have a hook at the proximal end and distal end. The gently curved hooks which can be straightened with a guide wire to facilitate insertion and removal of the stent are surprisingly effective in preventing migration and expulsion. The patented stents are widely accepted because they can be easily introduced both endoscopically and during open surgery.

All the commercially available stents have one disadvantage in common; the length of the available stents cannot be readily reduced to a shorter length desired by a surgeon without removing the means which reduce the tendency of the stent to migrate or to be expelled. As a result, the available stents have to be provided in a variety of predetermined lengths.

SUMMARY OF THE INVENTION

It is an object of the present invention to disclose a novel ureteral stent which can be supplied in a single length because it can be reduced in length without increasing the tendency for it to migrate or to be expelled when implanted.

The stent of the present invention comprises a flexible, elongated tubular member of substantially uniform outside surface throughout its length having a proximal end which is set in the form of a hook or loop a trimmable, distally extending elongated portion and means for forming a distal hook or similar retaining structure for reducing the tendency of the stent to migrate or be expelled.

In one embodiment, the means for forming the distal hook or similar structure is a second tubular member which has a preformed distal hook or similar retaining structure at one end and a connector for uniting the first and second tubular members at the other end.

In a second embodiment, the means comprises a reinforcing strip or wire embedded in the wall of the tubular member which permits the distal end of the member to be formed into a hook or loop which can be straightened with a guide wire and which will assume its hook or loop shape when the guide wire is removed.

In both embodiments the length of stent is shortened by cutting off the undesired length of the trimmable first member before forming the distal hook or similar retaining structure.

The stent is preferably made of a soft, flexible, radiopaque material and may be provided with indicating means which can be seen through a cystoscope and which will show the direction the proximal hook will extend when the stent is in place. The indicating means can also be used to help determine the proper length of the stent without the need for a separate measuring device.

When the desired length of the stent has been determined and a stent of the proper length constructed, the stent may be put in place by inserting a guide wire through a distal opening and into the lumen. If the proximal end of the stent is open the guide wire used for this purpose will have a leading end which is larger than the proximal end opening. The guide wire is inserted until the proximal hook is straightened. Because the guide wire is relatively stiff the distal hook also is straightened in the process. Next, a stent pusher is threaded over the free end of the guide wire behind the stent to aid the passage of the stent through a cystoscope. When the guide wire is removed the proximal and distal ends assume the shape of hooks or loops.

The above stated and other objects and advantages of the invention will be apparent from the description which follows:

DESCRIPTION OF THE DRAWINGS

FIG. 4 is an elevational view of a second embodiment of the present invention;

FIG. 5 is an enlarged sectional view of the stent taken along lines 5—5 of FIG. 4;

FIG. 6 is a view, similar to FIG. 5, of an embodiment in which the cross-section of the tubular member of FIG. 4 is ovate;

FIG. 7 is an enlarged view, partly in section, of the proximal end of the tubular member of FIG. 4;

FIGS. 8 and 9 are schematic views showing the distal end of the member of FIG. 4 being formed into a hook;

FIG. 10 is an enlarged exploded view, partly in section, of a newly formed hook at the distal end of the member of FIG. 4 and a cap for closing the open lumen at the distal end; and FIG. 11 is an enlarged view, with the cap of FIG. 10 in place in the open lumen of the distal end.

DESCRIPTION OF PREFERRED EMBODIMENT

Figure 1:
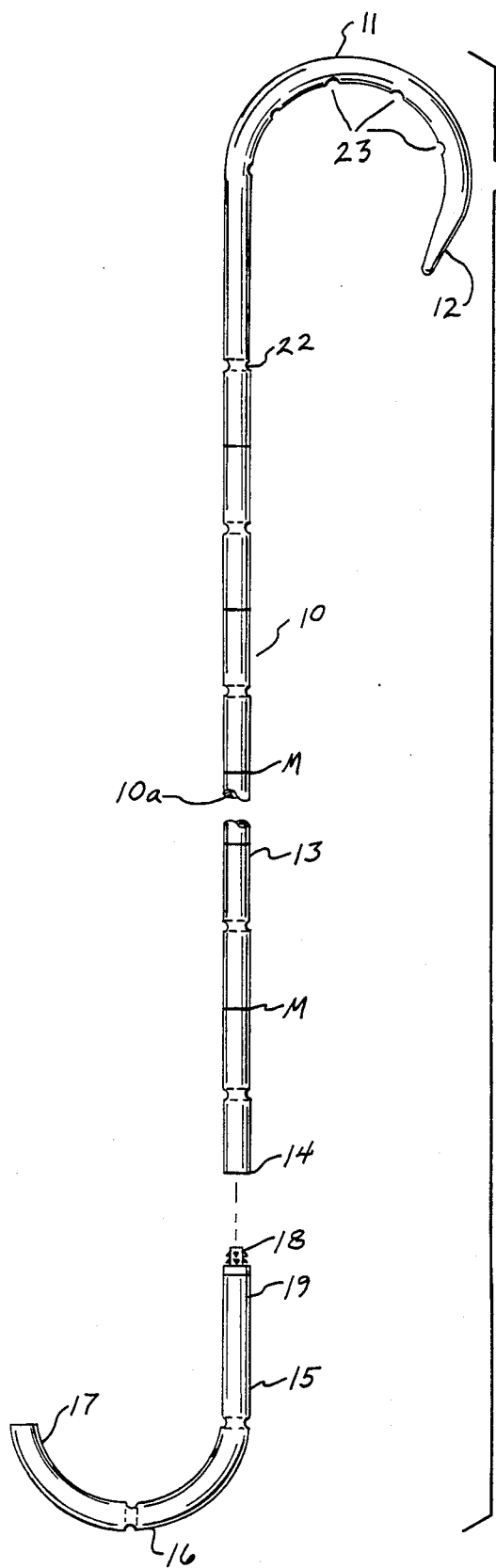
FIG. 1 is an elevational view of a first embodiment of the present invention which shows the first and second members which can be united to form a unitary stent.
Figure 2:
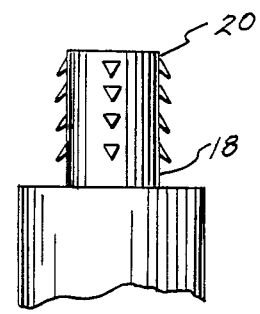
FIG. 2 is an enlarged view partly in section of the connector bearing end of the second member of FIG. 1.
Figure 3:
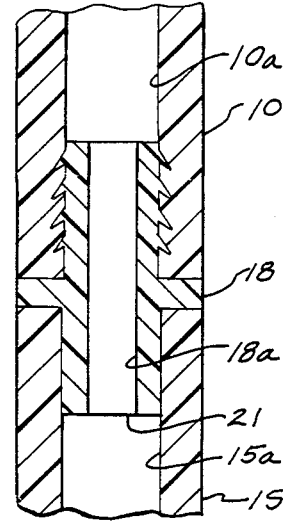
FIG. 3 is an enlarged sectional view showing the connector uniting the first and second members of FIG. 1 in to a unitary stent.

In the preferred embodiment shown in FIGS. 1 to 3, there is seen an elongated tubular first member 10 having a hook 11 at the proximal end 12, a generally straight trimmable portion 13 extending to the distal end 14 and a second member 15 having a hook 16 at one end 17 and a tubular connector 18 at the other end 19.

As best seen in FIGS. 2 and 3, the connector 18 which has a central lumen 18a and has barbs at one end 20. The other end 21 of the connector is glued or otherwise locked in the lumen 15a of the second tubular member 15. When the trimmable portion 14 has been cut to its desired length the barbed end 20 of the connection 18 is force fit into the lumen 10a of the new distal end of the first member 10 to form a unitary stent which resists separation.

The first member and the second member are preferably aligned prior to connection so that the proximal and distal hooks will extend in opposite directions so that when the unitary stent is used as an indwelling ureteral stent the proximal hook will be in the lower calix or renal pelvis while the distal hook will curve out into the bladder.

Referring back now to FIG. 1, it can be seen that the tubular member 10 has radial drainage passages 22 which connect the lumen 10a of the tubular member 10 to the outside and permit inside/ outside drainage. The drainage passages 22 are located about 5 centimeters apart on both sides of the trimmable portion 13 and the passages 22 of both sides are preferably aligned. It also can be seen that there are similar but larger openings 23 in the inside wall of the proximal hook 11.

The components of the first embodiment of the invention may be provided in a kit including one or more first and second tubular members, and the required guidewires. A stent pusher may be supplied as a component of the kit or a satisfactory stent pusher also may be made from a half length of a relatively stiff standard ureteral catheter, preferably 5 French.

The second embodiment of the invention is shown in FIGS. 4 to 11. As seen in FIG. 4 there is an elongated member 110 having a preformed hook 111 at the proximal end 112 and a generally straight trimmable portion 113 extending to the distal end 114.

As seen best in FIGS. 4 to 7 and 11, the trimmable portion 113 is reinforced with a wire 115, which is of a memory possessing material, such as spring wire, which can be formed into a distal hook or loop which can be straightened with a guide wire but will resume the hook or loop shape when the straightening force of the guide wire is removed. The wire 115, which can also be a strip, twisted strands or some other functional equivalent, is preferably embedded in the wall of the stent as seen in FIGS. 5 and 6. As seen in FIG. 7, the proximal hook 111 is preferably unreinforced, so that it is soft and yielding.

A stent of the desired length can be made from the member 110 by cutting off the unneeded length of trimmable portion 113 with a tool which will cut the wire 115. In calculating the length of the final stent enough extra length should be provided to permit a hook or loop to be formed in the distal end. As seen in FIGS. 8 and 9, the distal hook may be formed by inserting the new free distal end 112 of the trimmable portion 113 into a recess 116 in the hook forming tool 117 and then shaping the wire 115 in the distal end of the trimmable portion 113 to conform to exterior diameter of the tool 117.

If it is desired to close the end of the lumen, in the newly formed distal hook, a cap 118 such as that shown in FIGS. 10 and 11 can be used. The cap 118 is sized to be force fit into the lumen. If desired, the cap 118 can be of a magnetic material so that a magnetic retrieving tool can be used to remove the implanted stent.

A kit for the second embodiment might include the tubular member 110, the hook forming tool, the cap and, if desired, suitable means for cutting the reinforced trimmable portion.

The tubular members 10 and 110 are preferably provided with markings M which can be used to quickly calculate the desired length of the trimmable portion without the need for actual measuring. The tubular members 10, 15 and 110 may be provided when indentifying means, such as a colored strip, to show when the hooks are straightened, the direction they will curve when the straightening force is removed.

The tubular member(s) of the stent are made of a suitable flexible material such as nylon which is soft and stiff enough for the intended purpose and which preferably contains a radiopaque material. This allows the user to radiographically estimate the ureteral length and adjust length of the stent to the proper size for passage. The member(s) may be supplied in several sizes, such as 7 French and 8.5 French and a single length.

The stent is normally supplied with the proximal end closed so that a guide wire (not shown) can be used to insert the stent as described in U.S. Pat. No. 4,212,304.

However, it can be supplied with the proximal end open to help bypass obstructions. When the stent is supplied with both ends open, the proximal end opening is smaller than the distal end opening or the lumen. When an obstruction in the ureter is encountered that cannot be bypassed by the stent using the normal method of introduction, the stent is threaded on a small diameter guide wire which has a forgiving, unreinforced tip on its proximal end (not shown). The forgiving, unreinforced tip minimizes the possibility of damage being caused to the body by the guide wire. The tip and proximal end of the guide wire are passed through the proximal opening of the stent and maneuvered past the obstruction in the ureter. When it is known that the tip and the proximal end are safely past the obstruction, the stent is advanced over the guide wire past the obstruction and pushed into place with the stent pusher. The guide wire is then withdrawn and the stent pusher is disengaged from the stent. A replacement stent may be inserted by reinserting the guide wire, removing the original stent and running a new stent over the guide wire into place.

The proximal hook and distal length of the stent is preferably formed by extruding a length of tubing of the desired size and durometer. The proximal end of the tubing is then placed in a mold to close or reduce the size of the opening to less than the diameter of the guide wire to be used and the lumen. The length of tubing is then placed in a form to shape the proximal hook. The drainage openings may be formed at any step of the process by piercing the wall of the tubing with a flattened, sharpened hole cutter of the desired size or by use of a laser or any other conventional means. The second tubular member, if any, may be formed in a similar manner and the connector force fit or glued into place.

In the preferred embodiments described and shown in the drawing, the proximal and distal end portions of the stent are both in the form of gently curved hooks. However, it is to be understood that the term "hook" is intended to include other functionally equivalent shapes, including loops, which may prevent migration and do not increase the effective outer diameter of the stent, or complicate its method of introduction.

It will be readily apparent to those skilled in the art that a number of modifications and changes can be made without departing from the spirit of the invention. For example, although the term "wire" has been used to describe the reinforcing means in the second embodiment, it is to be understood that the term is intended to cover acceptable functional equivalents. Therefore, it is to be understood that the scope of the invention is not to be limited by the foregoing description, but only by the claims.

I claim:

1. An elongated member for use in preparing a custom length ureteral stent for a specific patient, said stent having hooks at the proximal and distal ends and an elongated intermediate section, said member having a preformed hook at the proximal end and an elongated, substantially straight distal end which is removable, said distal end including a reinforcing strip of spring wire in a wall thereof, said spring wire being trimmable and permitting said distal end to be readily formed into a second hook which can be straightened with a guide wire and which will resume its hook shape when the guide wire is removed.

2. A kit for preparing a custom length ureteral stent for a specific patient, said stent having proximal and distal hooks and an elongated intermediate section, said kit comprising a member having a hook at one end and an elongated substantially straight distal end which is removable, said distal end including a trimmable, reinforcing strip of spring wire in a wall thereof, said spring wire permitting said distal end to be formed into a second hook which can later be straightened and which will resume its hook shape when the straightening force is removed; and a tool for forming the distal end of the member containing the strip of spring wire into a hook.

* * * * *